United States Patent
Sojka et al.

(10) Patent No.: US 7,306,809 B2
(45) Date of Patent: *Dec. 11, 2007

(54) OPTICALLY ACTIVATED PARTICLES FOR USE IN COSMETIC COMPOSITIONS

(75) Inventors: Milan J. Sojka, Algonquin, IL (US); Lydia Ortega, Butler, NJ (US)

(73) Assignee: Lipo Chemicals, Inc., Paterson, NJ (US)

(*) Notice: Subject to any disclaimer, the term of this patent is extended or adjusted under 35 U.S.C. 154(b) by 746 days.

This patent is subject to a terminal disclaimer.

(21) Appl. No.: 10/243,060

(22) Filed: Sep. 13, 2002

(65) Prior Publication Data

US 2004/0052742 A1 Mar. 18, 2004

(51) Int. Cl.
*A61K 6/00* (2006.01)

(52) U.S. Cl. .............. 424/401; 424/489; 424/490

(58) Field of Classification Search ........ 424/401, 424/489, 490, 59, 60, 78.03, 69, 63
See application file for complete search history.

(56) References Cited

U.S. PATENT DOCUMENTS

| | | | |
|---|---|---|---|
| 4,752,496 A | 6/1988 | Fellows et al. | |
| 4,963,448 A | 10/1990 | Ichimura et al. | |
| 6,117,435 A | 9/2000 | Painter et al. | |
| 6,194,375 B1 * | 2/2001 | Ness et al. | 512/4 |
| 6,204,033 B1 | 3/2001 | Muller-Schulte | |
| 6,329,059 B1 | 12/2001 | Karchevsky et al. | |
| 6,586,013 B2 * | 7/2003 | Victor | 424/490 |
| 6,613,359 B2 * | 9/2003 | Victor | 424/489 |
| 6,752,002 B2 * | 6/2004 | Boltz | 424/401 |
| 2002/0007078 A1 | 1/2002 | Lin | |
| 2002/0131941 A1 | 9/2002 | Habeck et al. | |

FOREIGN PATENT DOCUMENTS

| | | | |
|---|---|---|---|
| CA | 1255603 | * | 6/1989 |
| EP | 0 460 994 | | 12/1991 |
| JP | 2001507384 | | 6/2001 |
| JP | 2001181132 | | 7/2001 |
| JP | 2002155189 | | 5/2002 |
| WO | WO 94/28223 | | 12/1994 |
| WO | WO 02/098274 | | 12/2002 |
| WO | WO 02/098349 | | 12/2002 |

OTHER PUBLICATIONS

LIPOLIGHT™ OAP/C Technical Bulletins, Lipo Chemicals, Inc., (Jun. 2002).

* cited by examiner

*Primary Examiner*—Michael P. Woodward
(74) *Attorney, Agent, or Firm*—Marshall, Gerstein & Borun LLP

(57) ABSTRACT

Optically activated particles for use in cosmetic and pharmaceutical compositions are disclosed. The optically activated particles include a solid substrate having a fluorescent compound fixed thereto, and coated or encapsulated with a transparent or translucent coating of crosslinked polyvinyl alcohol. The optically activated particles absorb light at a UV wavelength and emit visible light at longer wavelengths, and are able to both absorb and scatter light in a diffuse manner in order to reduce the visual perception of skin imperfections, including cellulite, wrinkles, shadows, skin discolorations, blotchiness, and mild scars.

20 Claims, 3 Drawing Sheets

OPTICALLY ACTIVATED PARTICLES FOR USE IN COSMETIC COMPOSITIONS

FIELD OF THE INVENTION

The present invention relates to optically activated particles for use in cosmetic compositions. The optically activated particles reduce the visual perception of skin imperfections. More particularly, the optically activated particles diffuse ambient light and emit visible light to reduce the visual perception of imperfections including, but not limited to, cellulite, wrinkles around the eyes and mouth, skin discoloration by veins and arteries, shadows, pores, mild scars, follicles, and blotchiness of the skin. The optically activated particles can be used in various cosmetic compositions, for example, skin lotions, creams, hair shampoos, body rinses, bath gels, skin cleansing agents, hair conditioners, skin coloring compositions, hair colorants, foundation liquids and powders (compressed or loose), toothpastes, oral rinses, topical medicaments, and skin treatment products.

BACKGROUND OF THE INVENTION

Natural-looking skin is influenced by a number of physiological and genetic factors. Standard definitions of beautiful skin include skin having a transparent quality with uniform undertones of color (e.g., rosy red cheeks). The basis of this natural-looking appearance is the skin structure itself. The outer layer of human skin is a semi-transparent layer termed the stratum corneum. The transparency of the stratum corneum permits observation of the deeper layers of skin, where blood vessels and pigments reside. The reddish hue of hemoglobin in the blood, and the brown/black hue of melanin, the primary skin pigment, combine to produce the skin color of an individual. In addition to skin having a transparent look with a uniform underlying color distribution, an ideal skin also should be smooth and even, with no apparent surface flaws. Very few individuals meet the ideal skin standard, therefore most individuals require assistance in the form of cosmetic compositions. Thus, a wide variety of "makeup" compositions have been developed to improve skin appearance.

Traditional makeup is not designed to mimic the natural appearance of beautiful skin, but is applied to the skin to mask skin imperfections. Currently, the trend in cosmetic composition is to provide a more natural-looking skin appearance. In particular, a long-sought goal is the development of a cosmetic composition that does not give the user a "made-up" look. However, it has been difficult to accomplish the goal of overcoming skin flaws and uneven skin tone, while maintaining the vibrant look of clean, bare skin. This difficulty is attributed primarily to opaque components typically included in cosmetic compositions, such as the titanium and iron oxide pigments, that provide the desired color and skin coverage, but obscure a vibrant skin transparency. Transparent pigments recently have become available, but the coverage needed to mask flaws in the skin surface frequently is lacking.

Personal care compositions have addressed the reduction of skin imperfections and the visible signs of aging, e.g., fine lines and wrinkles, using two major approaches. The first approach uses various bioactive antiaging ingredients. The second is a physical approach using inorganic materials to mask the appearance of fine lines and other skin imperfections. The second approach used is known as "soft focus" technology, which is based on the principle of scattered light. A recent third approach is to combine light scattering with fluorescent light emission. The emitted light illuminates the shadows in skin imperfections and provides an illusion that the imperfections do not exist.

The use of fluorescent brightener compounds in a cleansing and cosmetic compositions is known. U.S. Pat. No. 4,032,263 discloses a bleaching and brightening detergent composition containing an anionic and/or nonionic detergent, a builder salt, a peroxymonosulfate bleaching agent, a bromide bleaching promoter, and one or more optical brighteners that are stable in the presence of the bleach and the promoter.

U.S. Pat. No. 4,752,496 discloses a method of applying cosmetic ingredients to a substrate. The cosmetic ingredients are combined with a liquid carrier and film-forming agent, and deposited onto a substrate. The film-forming agent microencapsulates the cosmetic ingredients, and, after drying, protects the cosmetic ingredients. The protected cosmetic ingredients then can be applied to a substrate and covered with a paperboard sheet.

U.S. Pat. No. 6,117,435 discloses "natural-look" cosmetic compositions. These topical compositions for application to the skin contain silica beads having an inner silica core, a middle metal oxide layer, and an outer silica layer; at least one interference pigment; and, optionally, at least one noninterference pigment, in a cosmetically or pharmaceutically acceptable formula. The cosmetic compositions impart a natural appearance to the skin, while reducing the appearance of skin flaws or defects without an opaque or made-up appearance.

U.S. Pat. No. 6,194,375 discloses a perfume absorbed within polymeric particles that further have a polymeric coating on the particle surface. The polymer on the particle surface can be part of an encapsulating shell, and can be highly hydrolyzed polyvinyl alcohol (PVA). U.S. Pat. No. 6,204,033 discloses spherical PVA polymer particles that encapsulate a magnetic colloid for use in binding biomolecules. WO 94/28223 discloses nonwoven articles comprising a nonwoven web of organic fibers and a binder comprising at least partially cross-linked by a resin having a plurality of hydroxy groups.

Optically activated particles containing a fluorescent brightener fixed to a microporous nylon-12 powder core, and encapsulated in a polyoxymethylene urea (PMU) shell, are commercially available as LipoLight™ OAP/C from Lipo Chemicals, Inc., Paterson, N.J. The fluorescent intensities of the PMU encapsulated particles are about twice that of identical, but nonencapsulated, particles. The encapsulated particles are used to reduce the perception of skin imperfections. However, the PMU shell poses environmental and toxicity concerns because the presence of free formaldehyde. Accordingly, researchers have investigated particles that eliminate the use of PMU, while retaining the efficacy required to reduce the appearance of skin imperfections.

Accordingly, a need remains in the art for cosmetic compositions capable of imparting a perception that human skin has fewer wrinkles and other imperfections, e.g., cellulite, generates an even skin tone, obscures discolorations of the skin, and/or reduces skin blotchiness. The optically activated particles of the present invention meet this need by emitting and reflecting visible light, and increasing the diffusion of light. There also is a need to provide improved optically activated particles that overcome the disadvantage associated with prior optically activated particles.

SUMMARY OF THE INVENTION

The present invention is directed to optically activated particles useful in topically applied compositions, such as cosmetic compositions and pharmaceutical compositions. The optically activated particles reduce the visual perception of skin imperfections. More particularly, the present invention is directed to optically activating particles comprising a solid substrate have a fluorescent compound fixed thereto, and said fluorescent compound-treated substrate is encapsulated in, or coated by, a crosslinked polyvinyl alcohol (PVA).

The present invention provides optically activated (OA) particles for use in topically applied compositions to reduce the visual perception of skin imperfections by the emission of visible light and by light scattering. An optically activated particle comprises (a) a solid substrate, for example, a synthetic polymeric substrate, a natural polymeric substrate, an insoluble salt, a mineral, or other insoluble solid, and (b) a fluorescent compound permanently or semipermanently fixed to the solid substrate to form fluorescent compound-treated particles that are (c) encapsulated in a transparent crosslinked PVA shell.

The OA particles diffuse and emit visible light to reduce the visual perception of cellulite, shadows, skin discolorations, wrinkles, and similar skin imperfections. In particular, after the optically activated particles are topically applied to the skin surface, the encapsulated OA particles absorb a portion of the ultraviolet radiation and emit visible light to reduce the visual perception of skin imperfections.

The encapsulated OA particles are used in the preparation of topically applied compositions, such as skin lotions, creams, hair shampoos, body rinses, bath gels, skin-cleansing agents, hair conditioners, skin coloring compositions, hair colorants, foundation liquids and powders (compressed or loose), tooth pastes, oral rinses, topical medicaments, and skin treatment products.

Accordingly, one aspect of the present invention to provide encapsulated OA particles for use in topically applied compositions, wherein the OA particles scatter light at all wavelengths, and absorb ultraviolet light of particular wavelengths and emit visible light at longer wavelengths (i.e., release energy in the form of light), in order to reduce the visual appearance and perception of skin imperfections.

Another aspect of the present invention is to provide OA particles wherein the solid substrate is pretreated, for example, with a wetting or swelling agent, to render the solid substrate wettable, and electrostatically or ionically available for fixing a fluorescent compound thereto. In preferred embodiments, a swelling agent is used to swell a polymeric substrate for fixing a fluorescent compound to the substrate.

Another aspect of the present invention is to provide encapsulated OA particles having a fluorescent compound adhered or fixed to a solid substrate by one or more of Van Der Waal's forces, ionic bonding, covalent bonding, hydrogen bonding, or other strong or weak physical or chemical association, such that the fluorescent compound is permanently, or at least semipermanently, fixed to the solid substrate.

Another aspect of the present invention is to provide OA particles that are encapsulated with a transparent and/or translucent coating of cross-linked PVA. The encapsulated OA particles overcome disadvantages associated with PMU encapsulated OA particles, and surprisingly improve the efficacy of OA particles used in topically applied compositions.

Another aspect of the present invention is to provide encapsulated OA particles having a median particle size less than about 50μ (microns), preferably about 0.1μ to about 50μ, more preferably about 1μ to about 30μ, and most preferably about 2μ to about 15μ, in diameter. In preferred embodiments, an encapsulated OA particle of the present invention is colorless, transparent, or translucent, and has a sufficiently small particle size to avoid detection by a naked human eye.

Another aspect of the present invention is to provide encapsulated OA particles comprising a synthetic polymeric substrate selected from the group consisting of a nylon, an acrylate, a polyester a polyethylene, a polypropylene, a polyvinyl chloride, or a similar plastic-like polymer, and mixtures thereof.

Yet another aspect of the present invention is to provide encapsulated OA particles, wherein the solid substrate is in the form of, but not limited to, a sphere, a cube, a cylinder, a tetrahedroid (pyramidally shaped), a rhomboid, a plate, or other polygonal-shaped configuration; or other regularly or irregularly shaped particles. The solid substrate can be solid or hollow in structure.

These and other novel aspects and features of the present invention will become apparent from the following detailed description of the preferred embodiments, taken in conjunction with the accompanying drawings.

DETAILED DESCRIPTION OF THE PREFERRED EMBODIMENT

Figure 1:
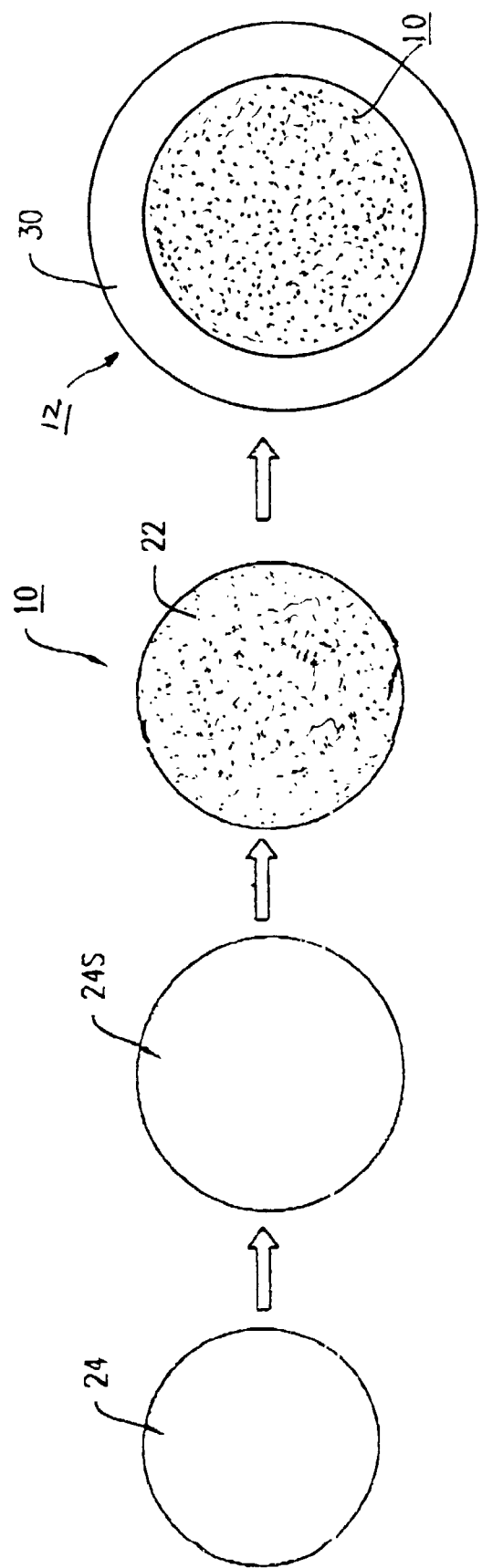
FIG. 1 is a schematic representation of the preparation of an encapsulated OA particle of the present invention.

Optically activated particles of the present invention emit and diffuse visible light to dramatically reduce the appearance of skin imperfections. The invisible micron-sized particles comprise a core of a fluorescent compound fixed to a solid substrate encapsulated by a crosslinked polyvinyl alcohol. The OA particles can be formulated into topically applied compositions, such as wrinkle creams, pressed and loose powders, foundations, and eye gels, to reduce the appearance of wrinkles, pores, and other skin imperfections.

The particles combine the effects of light emission, which illuminates shadows in the skin imperfection, and light scattering, which gives a soft-focus effect. The optical effect is attributed to a combination of diffuse light emission (i.e., fluorescence) and the scattering of visible light. In particular, the fluorescent compound fixed onto the solid substrate absorbs a portion of the invisible UV light and reemits that light as diffuse visible light. The emitted, visible light illuminates the shadowed areas of wrinkles, enlarged pores, and other skin imperfections, thus significantly reducing their appearance. The diffusion of the reflected incident visible light causes a soft-focus effect that contributes to the overall beneficial optical result. This combination of effects allows the OA particles to dramatically reduce the appearance of skin imperfections.

In particular, the optically activated particles are used in cosmetic compositions to reduce the visual perception of cellulite, shadows, wrinkles, mild skin discolorations, mild scars, varicose veins, and blotchiness of the skin, particularly, but not limited to, the face area. The particles preferably are colorless, transparent, or translucent, and have a sufficiently small particle size to be invisible to the naked human eye. The human eye perceives a combination of scattered and emitted light provided by the optically activated particles. The OA particles can be incorporated into gels, dispersions, emulsions, and powders, and compositions containing the OA particles can be used alone or over make-up compositions.

The substrate of the OA particles can be any solid material that is insoluble in the vehicle or carrier of the topically applied composition, and that is capable of having a fluorescent compound fixed permanently or semipermanently thereto. The fluorescent compound can be fixed to the solid substrate by one or more methods, such as Van Der Waal's forces, ionic bonding, covalent bonding, hydrogen bonding, or other physical and chemical association.

The substrate typically is a synthetic polymeric substrate, for example, a polyamide, a polyacetate, a polyester, a polyacrylic, a polyethylene, a polypropylene, a polyvinyl chloride, rayon, or other similar synthetic polymers. The substrate also can be other solid, materials, including, but not limited to, a natural polymeric material, e.g., cotton cellulose, regenerated cellulose, microcrystalline cellulose, starch, and similar natural fibers; an insoluble salt; a mineral; or any other insoluble solid material capable of acting both as a substrate for the fluorescent compound and as a scattering center. The term "insoluble" as used herein is defined as a substrate that is insoluble in the vehicle or carrier of a topically applied composition incorporating the present OA particles.

The solid substrate typically has a median particle size of less than about 50μ (microns) in diameter, and preferably about 0.1 to about 50μ in diameter. More preferably, the substrate has a median particle size diameter of about 1 to about 30μ, and most preferably about 2 to about 15μ. The solid substrate has a particle size range of about 0.001 to about 150μ. Preferably, the substrate is colorless, transparent, or translucent, and is sufficiently small in diameter to be invisible to the naked human eye.

The form or shape of the solid substrate is not limited. For example, the solid substrate can be a sphere, a cube, a cylinder, a tetrahedroid (pyramidally shaped), a rhomboid, a plate, or other polygonal-shaped configuration. The solid substrate particles also can be irregularly shaped, and, additionally, can be solid or hollow in structure.

One preferred solid substrate is nylon-12 or nylon-6 spheres having a median particle size diameter of about 5 to about 10 μm. Another preferred solid substrate is microcrystalline cellulose spheres.

A fluorescent compound is fixed to the solid substrate in an amount of about 0.01% to about 1%, and preferably about 0.02% to about 0.7%, by weight of the solid substrate. To achieve the full advantage of the present invention, about 0.05% to about 0.5%, by weight, of a fluorescent compound is fixed to the substrate.

As previously stated, the fluorescent compound is fixed to the substrate by one or more physical or chemical method. The fluorescent compound is fixed to the substrate either permanently (e.g., covalent bonding) or semipermanently (e.g., hydrogen bonding). A semipermanently fixed fluorescent compound remains fixed to the substrate throughout the manufacture, storage, and use of a topically applied composition containing the present OA particles.

The fluorescent compound can be fixed directly to the substrate. In another embodiment, the substrate can be swollen by a suitable solvent to assist fixing of the fluorescent compound on the substrate. The swelling solvent typically is an alcohol, diol, or polyol, e.g., a $C_{1-4}$ alcohol, like isopropyl alcohol, propylene glycol, ethylene glycol, a polyethylene glycol, butylene glycol, glycerol, and similar hydric solvents.

The identity of the fluorescent compound is not limited, and can be any compound capable of absorbing an invisible UV portion of the daylight spectrum, and converting this energy into the longer visible wavelength portion of the spectrum. The fluorescent compound is colorless on the substrate, and does not absorb energy in the visible part of the spectrum. The fluorescent compound typically is a derivative of stilbene or 4,4'-diaminostilbene, biphenyl, a 5-membered heterocycle, e.g., triazole, oxazole, or imidazole, or a 6-membered heterocycle, e.g., a coumarin, a naphthalamide, or an s-triazine.

One class of fluorescent compounds are the bistriazinyl derivatives of 4,4'-diaminostilbene-2,2'-disulfonic acid, exemplified in Table 1.

TABLE 1

| R | R' |
|---|---|
| —$NHC_6H_5$ | —$OCH_3$ |
| —$NHC_6H_5$ | —$NHCH_3$ |
| —$NHC_6H_5$ | —N(CH₃)(CH₂CH₂OH) |
| —$NHC_6H_5$ | —$N(CH_2CH_2OH)_2$ |
| —$NHC_6H_5$ | morpholino (—N(CH₂CH₂)₂O) |
| —$NHC_6H_5$ | —$NHC_6H_5$ |
| —NH—C₆H₄—SO₃H (para) | —$N(CH_2CH_2OH)_2$ |
| —NH—C₆H₄—SO₃H (meta) | —$N(CH_2CH_2OH)_2$ |
| —NH—C₆H₃(SO₃H)₂ | —$N(CH_2CH_3)_2$ |

Additional classes of fluorescent compounds are the 2-(stilben-4-yl)naphthotriazoles

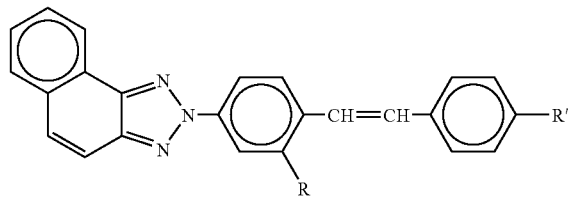

wherein R=—SO₃H, R'=H, and R=—CN and R'=—Cl;

the 2-(4-phenylstilben-4-yl)benzoxazoles

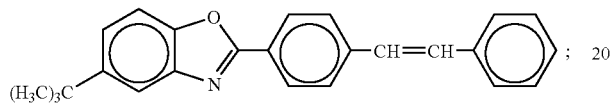

the bis(azol-2-yl)stilbenes

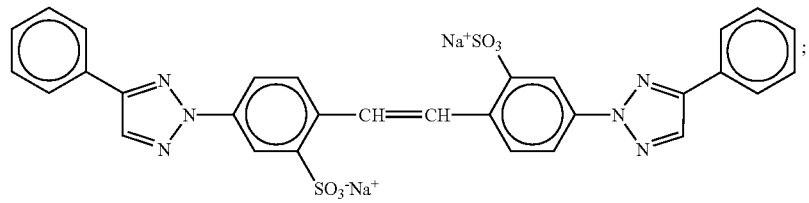

the 1,4-bis(styryl)benzenes

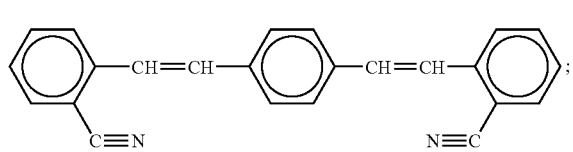

the 4,4'-bis(styryl)biphenyls

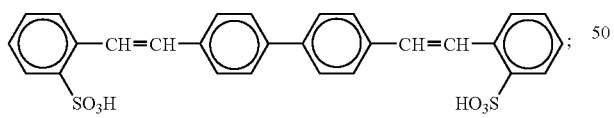

the 1,3-diphenyl-2-pyrazoline derivatives

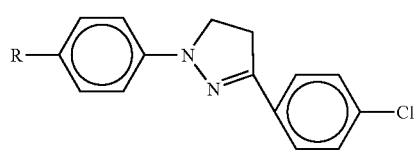

wherein R is —SO₃H, —SO₂NH₂, —SO₂NHCH₂CH₂CH₂N⁺(CH₃)₃·⁻ᔆᴼ₃OCH₃, —SO₂CH₂CH₂SO₃H, sodium salt, or

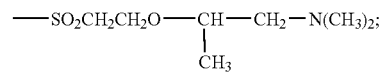

the bis(benzooxazol-2-yl) derivatives

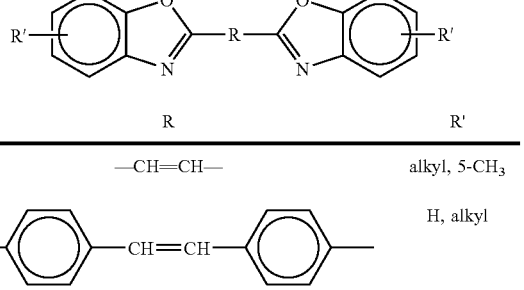

| R | R' |
|---|---|
| —CH=CH— | alkyl, 5-CH₃ |
| 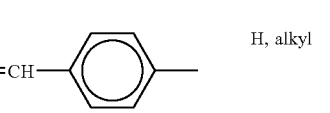 | H, alkyl |

-continued

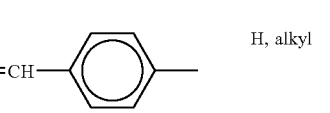

| R | R' |
|---|---|
|  | H, alkyl |
| 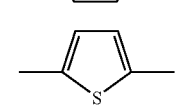 | COO-alkyl, SO₂-alkyl, H, alkyl | the bis(benzimidazol-2-yl) derivatives

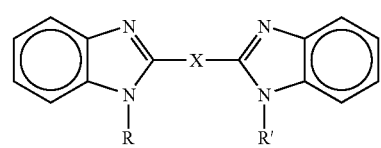

wherein X=—CH=CH— or

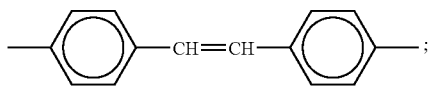

the 2-(benzofuran-2-yl)benzimidazoles; the coumarins, including 3-phenyl-7-aminocoumarin, 3-phenyl-7-(azol-2-yl) coumarins, 3,7-bis(azolyl)-coumarins,

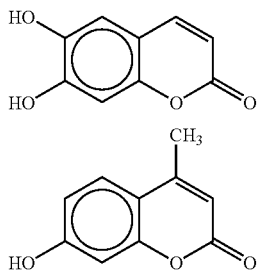

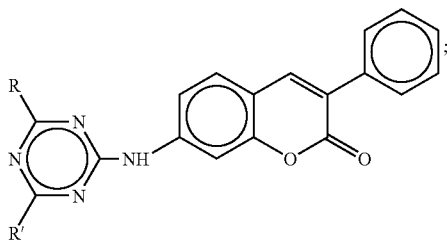

the carbostyrils

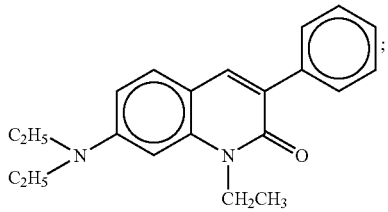

the naphthalimides

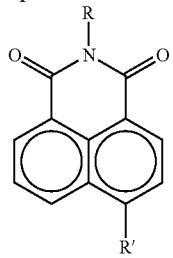

and miscellaneous compounds and classes such as quaternized pyridotriazoles, a pyrene compound

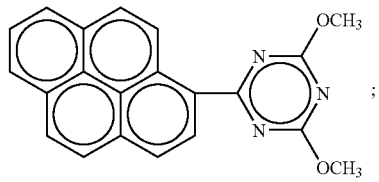

and the acylamino (R,R') derivative of 3,7-diamino-dibenzothiophene-2,8-disulfonic acid-5,5-dioxide, wherein preferred acyl groups are alkoxybenzoyls,

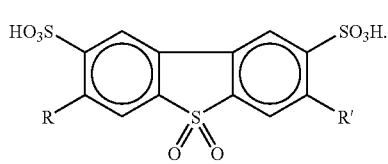

The fluorescent compounds are available under a variety of tradenames, such as TINOPAL, LEUCOPHOR, and CALCOFLUOR. Specific fluorescent compounds include, but are not limited to, TINOPAL 5BM, CALCOFLUOR CG, and LEUCOPHOR BSB.

After fixing the fluorescent compound to the solid substrate, the resulting fluorescent compound-treated substrate is coated by, or encapsulated in, a crosslinked PVA. The crosslinked PVA coating acts as an additional diffusing interface for emitted light, thereby increasing the diffusion of emitted and reflected light, which consequently reduces the visual perception of skin imperfections. The crosslinked PVA coating overcomes disadvantages associated with prior polyoxymethylene urea coatings on treated particles, and increases the efficacy of the OA particles.

The crosslinked polyvinyl alcohol is present in an OA particle of the present invention in an amount of about 0.01% to about 25%, and preferably about 0.05% to about 10%, by weight of the OA particle. To achieve the full advantage of the present invention, the crosslinked PVA is present in an amount of about 0.1% to about 5%, by weight of the OA particles.

Polyvinyl alcohol cannot be prepared directly by polymerization, and is obtained by the hydrolysis of polyvinyl acetate. The hydrolysis generally is stopped before completion, and polymers with varying amounts of hydrolysis are commercially available. A preferred polyvinyl alcohol used in the present OA particles has a substantial level of hydrolysis.

In particular, a polyvinyl alcohol that is about 70% to 100% hydrolyzed, i.e., in which about 70% to 100% of the acetate residues have been removed by hydrolysis, is preferred. More preferably, the polyvinyl alcohol is at least about 85%, preferably at least about 90%, and more preferably at least about 96% hydrolyzed, e.g., about 96% to 100% hydrolyzed.

In addition, a copolymer of polyvinyl alcohol, available through hydrolysis of the corresponding copolymer of vinyl acetate, can be used to encapsulate the treated particles. For example, a copolymer of vinyl acetate and vinyl formamide, with a high proportion of vinyl acetate can be hydrolyzed to a copolymer of vinyl alcohol and vinyl formamide.

Polyvinyl alcohol is a water-soluble or dispersible polymer. Therefore, in accordance with an important feature of the present invention, the PVA is crosslinked to provide an insoluble coating. The PVA is crosslinked using methods well known in the art, e.g., using a di- or polyfunctional cross-linking agent, gamma radiation, or freeze-thaw cycles. In particular, the PVA crosslinking agent can be, but is not limited to:

(a) disulfonate esters, for example, compounds of the formula

wherein p is a number from 2 to 12, and Y, independently, is tosylate, mesylate, or other alkyl or aryl sulfonate esters;

(b) multifunctional aziridines;

(c) multifunctional aldehydes, for example, glutaraldehyde, trioxane, paraformaldehyde, terephthaldehyde, malonaldehyde, and glyoxal, and acetals and bisulfites thereof;

(d) halohydrins, such as epichlorohydrin;

(e) multifunctional epoxy compounds, for example, ethylene glycol diglycidyl ether, bisphenol A diglycidyl ether, and bisphenol F diglycidyl ether;

(f) multifunctional carboxylic acids and esters, acid chlorides, and anhydrides derived therefrom, for example, di- and polycarboxylic acids containing 2 to 12 carbon atoms, and the methyl and ethyl esters, acid chlorides, and anhydrides derived therefrom, such as oxalic acid, adipic acid, succinic acid, dodecanoic acid, malonic acid, and glutaric acid, and esters, anhydrides, and acid chlorides derived therefrom;

(g) organic titanates, such as TYZOR AA, available from E. I. DuPont de Nemours, Wilmington, Del.;

(h) melamine resins, such as the CYMEL resins available from Cytec Industries, Wayne, N.J.;

(i) hydroxymethyl ureas, such as N,N-dihydroxymethyl-4-,5-dihydroxyethylene urea;

(j) multifunctional isocyanates, such as toluene diisocyanate, isophorone diisocyanate, methylene diisocyanate, xylene diisocyanate, and hexamethylene diisocyanate; and (k) other crosslinking agents for hydroxy containing polymers known to persons skilled in the art.

A preferred PVA crosslinking agent is a multifunctional aldehyde, in particular, glyoxal.

The OA particles also can contain optional ingredients, either beneath the crosslinked PVA shell, or applied to the crosslinked PVA shell. The optional ingredients can be a cosmetic ingredient, e.g., a skin colorant, skin conditioner, retinol, a protein, a vitamin, and the like, or can be a topical medicament, e.g., an antiacne medicament, an antibacterial agent, a sunscreen agent, a skin rash or skin disease medication, an antiitch compound, an antifungal compound, and the like.

Figure 2:
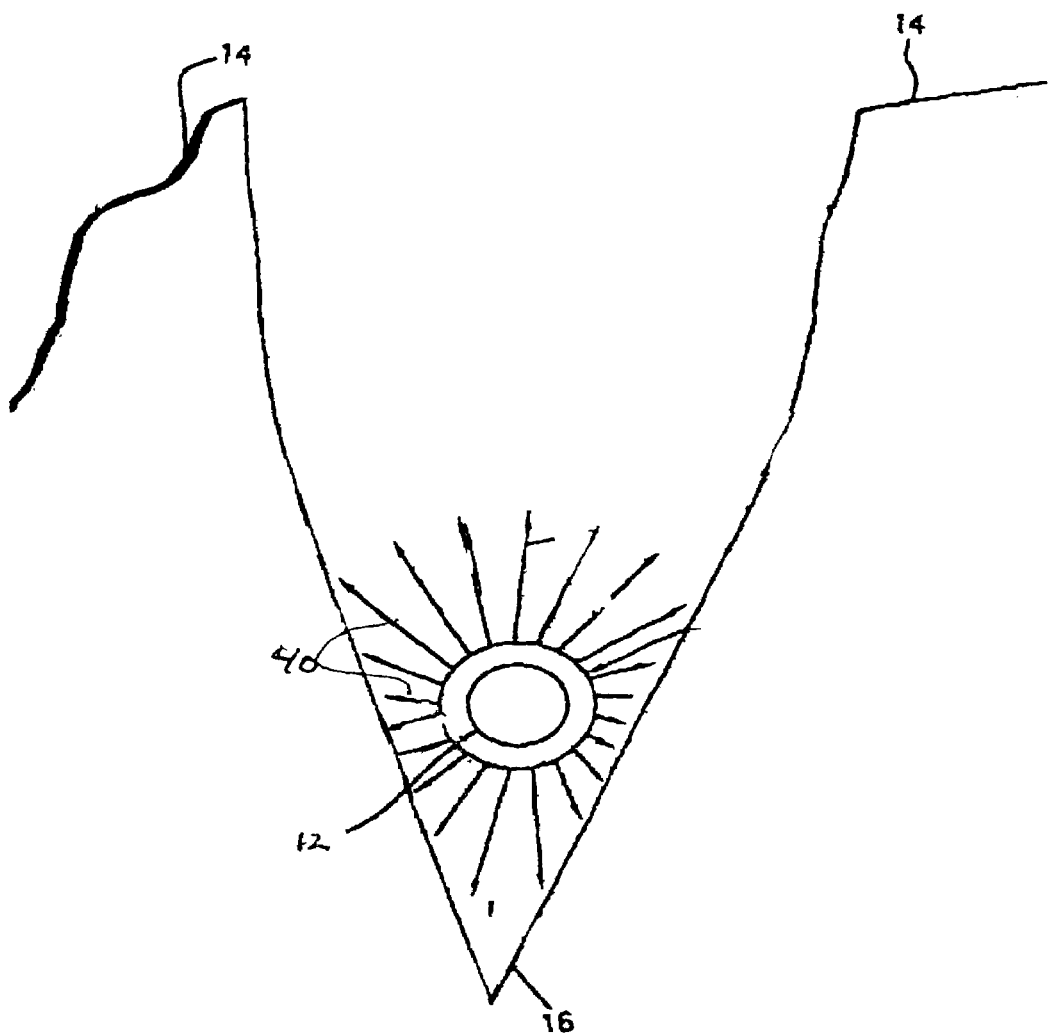
FIG. 2 is an enlarged schematic view of a present encapsulated optically activated particle within a crease of an outer skin layer, wherein the encapsulated optically activated particle is diffusing and emitting light to decrease the shadow effect of the skin imperfections.
Figure 3:
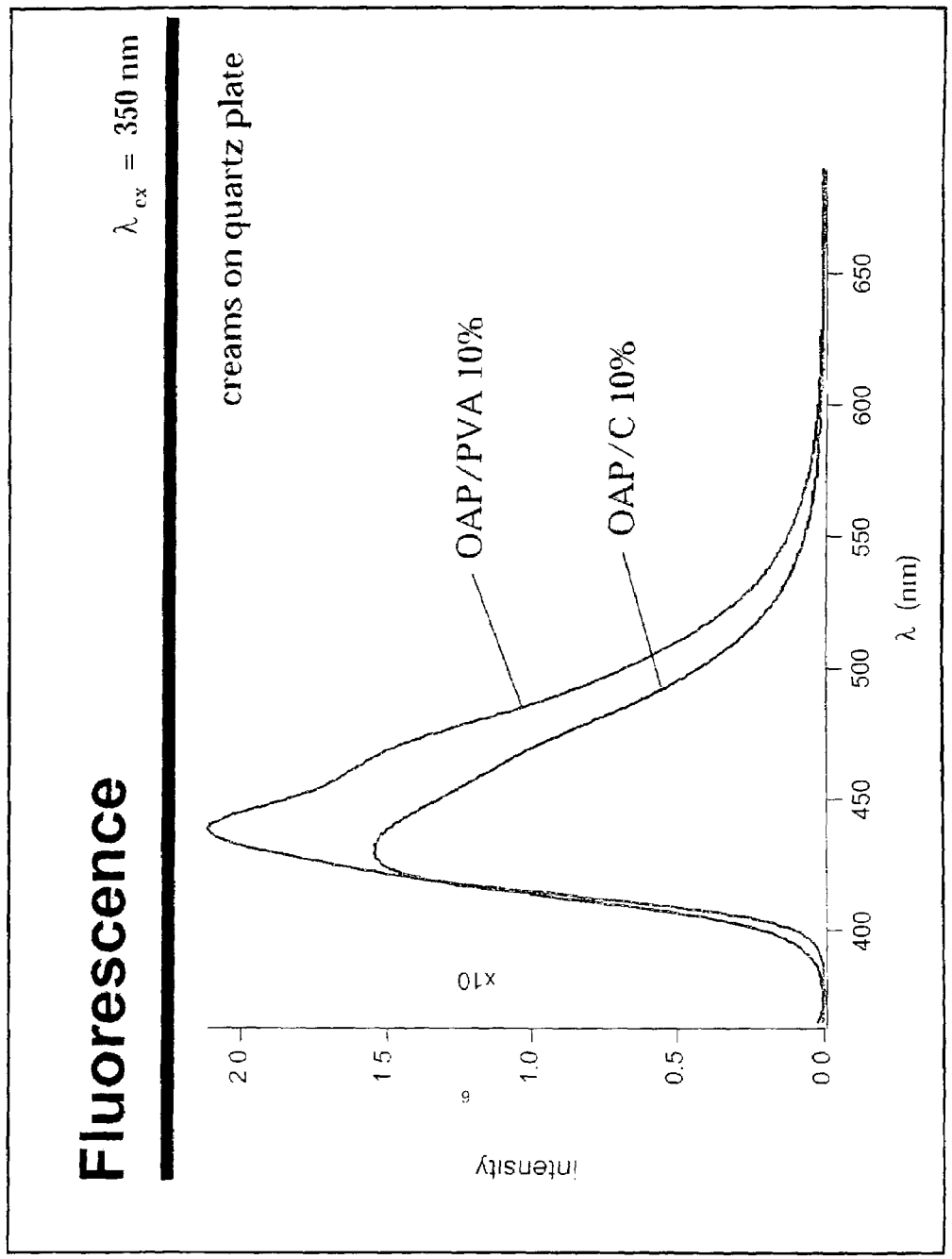
FIG. 3 contains plots of intensity versus wavelength (λ) comparing OA particles of the present invention to OA particles coated with PMU.

The present OA particles for use in topically applied compositions are represented in detail in FIGS. 1 through 3. The OA particles emit and diffuse light for to reduce the visual perception of cellulite, wrinkles, shadows, pores, follicles, skin discolorations by veins and arteries, and to obscure visual imperfections of the skin surface. Further, the OA particles reduce the perception of minor scars or abrasions, and blotchiness of the skin, for example, in the face area.

An optically activated particle 12 of the present invention is illustrated and prepared as shown in FIG. 1. In the preparation of the OA particles, a fluorescent compound 22 is fixed on a solid substrate 24, or an optionally swollen solid substrate 24S. Fluorescent compound 22 is fixed to substrate 24 (e.g., a nylon sphere) by covalent bonding, ionic bonding, Van Der Waal's forces, hydrogen bonding, or other strong or weak physical or chemical association, such that fluorescent compound 22 is fixed, permanently or semipermanently, to substrate 24 or 24S and becomes part of a fluorescent compound-treated particle 10.

When using a sphere as the substrate 24 or 24S, the optically activated particle 12 diffuses light 40 in a radially extending pattern, as shown in FIG. 2. A fluorescent compound-treated particle 10 is encapsulated within a transparent or translucent coating 30 of crosslinked polyvinyl alcohol. Thus, the optically activated particles 12 reduce the visual perception of cellulite, wrinkles, discoloration, or shadows 16 when applied to a skin surface 14, as depicted in FIG. 4.

Optically activated particles of the present invention can be prepared as follows:

EXAMPLES

Propylene glycol (875 g) and PEG 200 (125 g) were added to a 3-L round-bottomed flask equipped with a stirrer, condenser, and heating mantle. Nylon-12 powder (7μ in diameter) was added to the reaction mixture slowly over 15 minutes. The mixture was stirred for an additional 15 minutes to swell the nylon particles, then LEUCOPHOR BSB solution (commercially available from Clariant, 50 g) was added, and the resulting mixture was stirred at room temperature for 10 minutes. Distilled water (950 g) then was added, and the resulting mixture was slowly heated to 90° C. with a ramp rate of 1-2° C./min. The temperature was maintained at 90° C. for 30 minutes, then allowed to cool to room temperature. The mixture was filtered, and the collected white powder was washed with four 1200 mL portions of distilled water, then air dried to yield a wet powder. The wet powder was dried in an oven at 75° C. for 15 hours to yield a dry white fluorescent powder. Spectrophotometric analysis of the wash solutions indicated that the nylon particles contained 0.3% fluorescent compound.

Example 2

The procedure of Example 1 was repeated except the reaction temperature was raised to 100° C. Analysis indicated that the nylon particles contained 0.4%, by weight, fluorescent compound.

Example 3

The procedure of Example 2 was repeated except nylon-6 powder was used instead of nylon-12 powder. Analysis indicated that the nylon particles contained 0.5%, by weight, fluorescent compound.

Example 4

The procedure of Example 2 was repeated except ethylene glycol (1000 g) was substituted for the propylene glycol and PEG 200 mixture and no water was added. Analysis indicated that the nylon particles contained 0.4%, by weight, fluorescent compound.

Example 5

The procedure of Example 2 was repeated except butylene glycol (1000 g) was substituted for the propylene glycol and PEG 200 mixture and no water was added. Analysis indicated that the nylon particles contained 0.4%, by weight, fluorescent compound.

Example 6

The procedure of Example 2 was repeated except microcrystalline cellulose powder was used instead of nylon-12 powder. Analysis indicated that the microcrystalline cellulose powder contained 0.3%, by weight, fluorescent compound.

Example 7

Isopropyl alcohol (150 g) was added to a 1-L round bottom flask equipped with a stirrer, condenser, and heating mantle. Nylon-12 powder (7μ in diameter) was added to the reaction mixture slowly over 15 minutes and the mixture was stirred for an additional 15 minutes to swell the nylon particles. The mixture was filtered, and the filter cake containing approximately 80 g of isopropyl alcohol and the nylon powder was returned to the reaction flask. Distilled water (312 g) and LEUCOPHOR BSB solution (commercially available from Clariant, 8 g) was added, and the mixture was stirred at room temperature for 10 minutes. The resulting mixture was heated to 88° C. for 30 minutes, then allowed to cool to room temperature. The mixture was filtered, and the collected white powder was washed with four 200 mL portions of distilled water, the air dried to yield a wet powder. The wet powder was dried in an oven at 75° C. for 15 hours to yield a dry white fluorescent powder. Spectrophotometric analysis of the wash solutions indicated that the nylon particles contained 0.3% fluorescent compound.

Example 8

Polyvinyl alcohol (PVA) (CELVOL 165, 10 g degree of hydrolysis:99.3+%) was dispersed in 90 g of cold water at a temperature of 20-25° C. The resulting suspension then was heated to 95° C. as rapidly as possible under continuous stirring. At 95° C., the PVA dissolved completely, without residual particulates, in a maximum of 45 minutes. The mixture was cooled to room temperature, and a biocide was added to prevent microbial growth during storage.

A portion of the PVA solution was added to cold water to give a total PVA concentration of 0.2 weight % in a 2000 ml three-necked flask equipped with a stirrer, thermometer, and a condenser.

A dispersion of 35 weight % particles of Example 7 in 10.5 weight % water was added slowly to the stirred 0.2 weight % aqueous PVA solution. After the mixture in the reaction vessel was homogeneous, 1.25 weight % glyoxal was added, and heating was commenced. The reaction mixture was heated to 55° C. and the temperature was held for an hour to complete PVA crosslinking and provide a crosslinked PVA membrane on each particle. The resulting OA particles were filtered and dried. Scanning Electron Microscopy (SEM) and Electron Spectroscopy for Chemical Analysis (ESCA) indicate total encapsulation of the fluorescent-treated substrate particles.

The OA particles of the present invention are incorporated into liquid and solid topically applied compositions. The OA particles are incorporated into liquid topically applied compositions in an amount of about 0.5% to about 20%, and preferably about 1% to about 15%, by weight, of the composition. To achieve the full advantage of the present invention, the OA particles are incorporated in an amount of about 2% to about 12%, by weight, of the composition.

The OA particles are incorporated into solid topically applied compositions in an amount of about 0.5% to about 50%, and preferably about 1% to about 30%, by weight, of the composition. To achieve the full advantage of the present invention, the OA particles are incorporated in an amount of about 2% to about 20%, by weight, of the composition.

Example 9

A skin cream containing the optically activated fixed particles of Example 8 was prepared according to the following procedure:

| SEQ | Weight Percent | Ingredient | INCI Name |
|---|---|---|---|
| 1 | 77.15 | Deionized water | Water |
| 1 | 1.00 | UNIPHEN[1]) P-23 | Phenoxyethanol (and) Methylparaben (and) Ethylparaben (and) Propylparaben (and) Butylparaben |
| 1 | 0.35 | KELTROL[2]) CG | Xanthan Gum |
| 2 | 4.00 | LIPOVOL[3]) SES | Sesame (*Sesamum Indicum*) Oil |
| 2 | 0.50 | LIPOPEG[3]) 6000DS | PEG-150 Distearate |
| 2 | 1.25 | LIPOCOL[3]) C | Cetyl Alcohol |
| 2 | 2.50 | LIPONATE[3]) CG | Caprylic/Capric Triglyceride |
| 2 | 0.75 | LIPOWAX[3]) P | Cetearyl Alcohol (and) Polysorbate 60 |
| 2 | 2.50 | LIPO[3] GMS 450 | Glyceryl Stearate |
| 3 | 10.00 | Optically Activated Particles of Example 8 | |

[1])Available from InduchemAG, Switzerland;
[2])Available from Kelco Co., San Diego, CA;
[3])Available from Lipo Chemicals, Inc., Paterson, NJ.

Procedure

1. In a beaker, the ingredients of sequence #1 were heated to 78-80° C. with high sheer propeller mixing at medium/high speed.
2. In a separate beaker, the ingredients of sequence #2 were mixed and heated to 80° C.
3. The mixtures of steps 1 and 2 were combined using medium/high speed high sheer propeller mixing. Mixing was continued for 5 minutes or until emulsification was complete.
4. Cool to 25° C.
5. Add the ingredient of sequence #3, and mix until homogenous.

The resulting cosmetic cream was tested for fluorescence intensity and compared with the standard cream, which contained OA particle coated with polyoxymethylene urea. Surprisingly, the PVA-encapsulated particles outperformed the PMU encapsulated particles, as illustrated in FIG. 3. Accordingly, the present OA particles outperform prior OA particles, i.e., intensity is increased to 2.2 a.u. from 1.6 a.u., and the disadvantages associated with PMU, e.g., free formaldehyde, are overcome.

When optically activated particles 12 are exposed to ambient UV light, the particles absorb a portion of the UV light as energy, and release this energy as visible light 40, as shown in FIG. 2. Thus, fixing a fluorescent compound 22 to the solid substrate 24 provides a radiant emissive source of visible light 40. While not intending to be limited by theory, it is believed that the amount of visible light 40 is very small, and is not consciously perceived by the viewer, but is detected by the visual cortex. Thus, particles 12 perform an optical function that obscures skin imperfections and reduces the visual perception of skin imperfections.

OA particles of the present invention are encapsulated in a transparent or translucent shell of crosslinked PVA. Fluorescence intensities of encapsulated particles are more than double that of unencapsulated corresponding particles. While not wanting to be limited by theory, it is believed that the PVA shell acts as a diffusion lens to increase the effective diffusion pattern of visible light 40, which further reduces the visual perception of skin imperfections without regard to the configuration of the skin surface 14. Another nonlimiting theory is that the PVA encapsulation acts as a lens to focus incident UV light, and thus increase fluorescence. The PVA shell used in the present invention overcomes problems associated with prior polyoxymethylene urea coatings, and improves efficacy of the OA particles.

Accordingly, the present invention provides optically activated particles for use in topically applied compositions, wherein the optically activated particles are able to absorb light energy at one wavelength (e.g., about 350 nm) and emit and diffuse light at a different visible wavelength (i.e., releases energy in the form of light at about 400 to about 450 nm) in order to reduce the appearance and visual perception of skin imperfections, including shadows, skin discolorations, wrinkles, and cellulite, when applied to the skin surface. The OA particles also help obscure the skin beneath the particles.

The optically activated particles can be used in various cosmetic compositions, such as, but not limited to, skin lotions, creams, hair shampoos, body rinses, bath gels, skin-cleansing agents, hair conditioners, skin coloring compositions, hair colorants, foundation liquids and powders (compressed or loose), toothpastes, oral rinses, topical medicaments, and skin treatment products.

Many modifications and variations of the invention as hereinbefore set forth can be made without departing from the spirit and scope thereof. Therefore, only such limitations should be imposed as are indicated by the appended claims.

What is claimed is:

1. An optically activated particle comprising
   (a) a solid substrate;
   (b) a fluorescent compound fixed on the solid substrate; and
   (c) a crosslinked polyvinyl alcohol shell covering the solid substrate and fluorescent compound.

2. The particle of claim 1 wherein the solid substrate comprises a synthetic polymeric substrate, a natural polymeric material, an insoluble salt, a mineral, or a mixture thereof.

3. The particle of claim 2 wherein the solid substrate comprises a synthetic polymeric substrate selected from the group consisting of a polyamide, a polyacetate, a polyester, a polyacrylic, a polyethylene, a polypropylene, a rayon, a polyvinyl chloride, and mixtures thereof.

4. The particle of claim 2 wherein the solid substrate comprises a natural polymeric material selected from the group consisting of cellulose, regenerated cellulose, starch, a microcrystalline cellulose, and mixtures thereof.

5. The particle of claim 1 wherein the solid substrate has a median particle size of about 0.1 to about 50 microns in diameter.

6. The particle of claim 1 wherein the solid substrate has a median particle size of about 2 to about 15 microns in diameter.

7. The particle of claim 1 wherein the substrate, solid or hollow, is a sphere, a cube, a cylinder, a tetrahedroid, a rhomboid, a plate, or is irregularly shaped.

8. The particle of claim 1 wherein the substrate is a solvent swollen substrate, said solvent comprising an alcohol, diol, polyol, or mixtures thereof.

9. The particle of claim 1 wherein the fluorescent compound is present in an amount of about 0.01% to about 1%, by weight of the solid substrate.

10. The particle of claim 1 wherein the fluorescent compound is present in an amount of about 0.05% to about 0.5%, by weight of the solid substrate.

11. The particle of claim 1 wherein the fluorescent compound is selected from the group consisting of a 4,4'-diaminostilbene-2,2'-disulfonic acid, a 2-(stilben-4-yl)naphthotriazole, a 2-(4-phenylstilben-4-yl)benzoxazole, a bis-(azol-2-yl)stilbene, a 1,4-bis(styryl)benzene, a 4,4'-bis(styryl)biphenyl, a 1,3-diphenyl-2-pyrazoline, a bis(benzooxazol-2-yl), a bis(benzimidazol-2-yl), a 2-(benzofuran-2-yl)benzimidazole, a coumarin, a carbostyril, a naphthalimide, a quaternized pyridotriazole, a pyrene compound, a 3,7-diaminodibenzothiophene-2,8-disulfonic acid-5,5-dioxide, and mixtures thereof.

12. The particle of claim 1 wherein the crosslinked polyvinyl alcohol is about 70% to 100% hydrolyzed.

13. The particle of claim 1 wherein the crosslinked polyvinyl alcohol is present in an amount of about 0.01% to about 25%, by weight of the particle.

14. The particle of claim 1 wherein the crosslinked polyvinyl alcohol is crosslinked by a multifunctional aldehyde.

15. A topically applied composition comprising optically activated particles of claim 1.

16. The composition of claim 15 wherein the composition is a liquid comprising about 0.5% to about 20% of the optically activated particles, by weight of the composition.

17. The composition of claim 15 wherein the composition is a solid comprising about 0.5% to about 50% of the optically activated particles, by weight of the composition.

18. The composition of claim 15 selected from the group consisting of a skin lotion, a cream, a hair shampoo, a body rinse, a bath gel, a skin-cleansing agent, a hair conditioner, a skin coloring composition, a hair colorant, a foundation liquid, a foundation powder, a topical skin treatment.

19. A method of reducing a visual perception of skin imperfections comprising topically applying optically activated particles of claim 1 to human skin.

20. The method of claim 19 wherein the skin imperfection is selected from the group consisting of wrinkles, cellulite, skin discoloration, shadows, pores, scars, varicose veins, follicles, and blotchiness.

* * * * *

UNITED STATES PATENT AND TRADEMARK OFFICE
CERTIFICATE OF CORRECTION

PATENT NO. : 7,306,809 B2 Page 1 of 1
APPLICATION NO. : 10/243060
DATED : December 11, 2007
INVENTOR(S) : Milan Sojka et al.

It is certified that error appears in the above-identified patent and that said Letters Patent is hereby corrected as shown below:

On the Title Page:

Item (75), first named Inventor, "Milan J. Sojka" should be -- Milan F. Sojka --.

Item (73), "Lipo Chemicals, Inc." should be -- Lipo Chemicals Inc. --.

Signed and Sealed this

Twenty-first Day of October, 2008

JON W. DUDAS
*Director of the United States Patent and Trademark Office*